(12) United States Patent
Bobst

(10) Patent No.: US 8,137,324 B2
(45) Date of Patent: Mar. 20, 2012

(54) SYRINGE WITH INTERNAL SAFETY DEVICE

(75) Inventor: Benjamin Bobst, Mittelbiberach (DE)

(73) Assignee: Arzneimittel GmbH Apotheker Vetter & Co. Ravensburg, Ravensburg (DE)

( * ) Notice: Subject to any disclaimer, the term of this patent is extended or adjusted under 35 U.S.C. 154(b) by 327 days.

(21) Appl. No.: 11/990,314

(22) PCT Filed: Aug. 10, 2006

(86) PCT No.: PCT/EP2006/007927
§ 371 (c)(1),
(2), (4) Date: Feb. 11, 2008

(87) PCT Pub. No.: WO2007/017281
PCT Pub. Date: Feb. 15, 2007

(65) Prior Publication Data
US 2009/0227957 A1 Sep. 10, 2009

(30) Foreign Application Priority Data
Aug. 11, 2005 (DE) .......................... 10 2005 037 962

(51) Int. Cl.
*A61M 5/315* (2006.01)
*A61M 5/00* (2006.01)

(52) U.S. Cl. ......... 604/220; 604/110; 604/208; 604/222

(58) Field of Classification Search .................. 604/187, 604/208, 218, 220, 225
See application file for complete search history.

(56) References Cited

U.S. PATENT DOCUMENTS

| | | | | | |
|---|---|---|---|---|---|
| 772,114 | A | * | 10/1904 | Pappenheim | 604/220 |
| 1,130,493 | A | * | 3/1915 | Dickinson | 604/220 |
| 1,142,682 | A | * | 6/1915 | Dickinson | 604/220 |
| 1,343,787 | A | * | 6/1920 | Ewell | 604/220 |
| 1,496,654 | A | * | 6/1924 | Crowther | 604/220 |
| 1,526,056 | A | * | 2/1925 | Eisele | 604/220 |
| 1,540,215 | A | * | 6/1925 | Klett | 604/220 |
| 1,646,256 | A | * | 10/1927 | Patten | 604/220 |
| 1,649,022 | A | * | 11/1927 | Eisele | 604/220 |
| 1,678,991 | A | * | 7/1928 | Marschalek | 604/220 |
| 1,703,427 | A | * | 2/1929 | Langbein | 604/220 |
| 1,798,116 | A | * | 3/1931 | Brockway | 604/220 |
| 1,834,713 | A | * | 12/1931 | Benjamin | 604/220 |
| 1,838,039 | A | * | 12/1931 | Montuori | 604/220 |

(Continued)

FOREIGN PATENT DOCUMENTS

DE  2 222 713  8/1973

(Continued)

*Primary Examiner* — Kevin C Sirmons
*Assistant Examiner* — William Carpenter
(74) *Attorney, Agent, or Firm* — Harness, Dickey & Pierce, P.L.C.

(57) ABSTRACT

A syringe includes a syringe cylinder, a sealing plug movably disposed within the syringe cylinder, and with a plunger cooperating with the sealing plug. A safety device prevents a sliding back of the sealing plug within the syringe cylinder in any position the sealing plug assumes within the syringe cylinder. The safety device has a locking element which engages at the plunger in any position the plunger assumes within the syringe cylinder. The locking element is attached to a retaining fixture and protrudes from the retaining fixture same such that an attachment point of the locking element is closer to the sealing plug at the retaining fixture than the free end of the locking element opposite of the attachment point.

24 Claims, 1 Drawing Sheet

U.S. PATENT DOCUMENTS

| | | | | |
|---|---|---|---|---|
| 1,863,785 | A | * | 6/1932 | Dickinson ..................... 604/207 |
| 2,014,493 | A | * | 9/1935 | Eisele ........................... 604/220 |
| 2,015,970 | A | * | 10/1935 | Schoene ....................... 604/225 |
| 2,489,040 | A | * | 11/1949 | Lawshe ......................... 604/220 |
| 3,598,120 | A | | 8/1971 | Mass |
| 4,072,149 | A | | 2/1978 | Tischlinger |
| 4,589,870 | A | | 5/1986 | Citrin et al. |
| 5,222,945 | A | * | 6/1993 | Basnight ...................... 604/110 |
| 5,380,295 | A | | 1/1995 | Vacca |
| 5,803,918 | A | * | 9/1998 | Vetter et al. .................. 604/110 |
| 6,280,418 | B1 | | 8/2001 | Reinhard et al. |
| 2004/0122361 | A1 | | 6/2004 | Hart et al. |

FOREIGN PATENT DOCUMENTS

| | | |
|---|---|---|
| DE | 44 34 644 A1 | 4/1996 |
| DE | 694 17 340 T2 | 4/1999 |
| FR | 529 263 | 11/1921 |
| FR | 534 030 | 3/1922 |
| WO | 94/13339 A | 6/1994 |
| WO | 96/39214 A | 12/1996 |

* cited by examiner

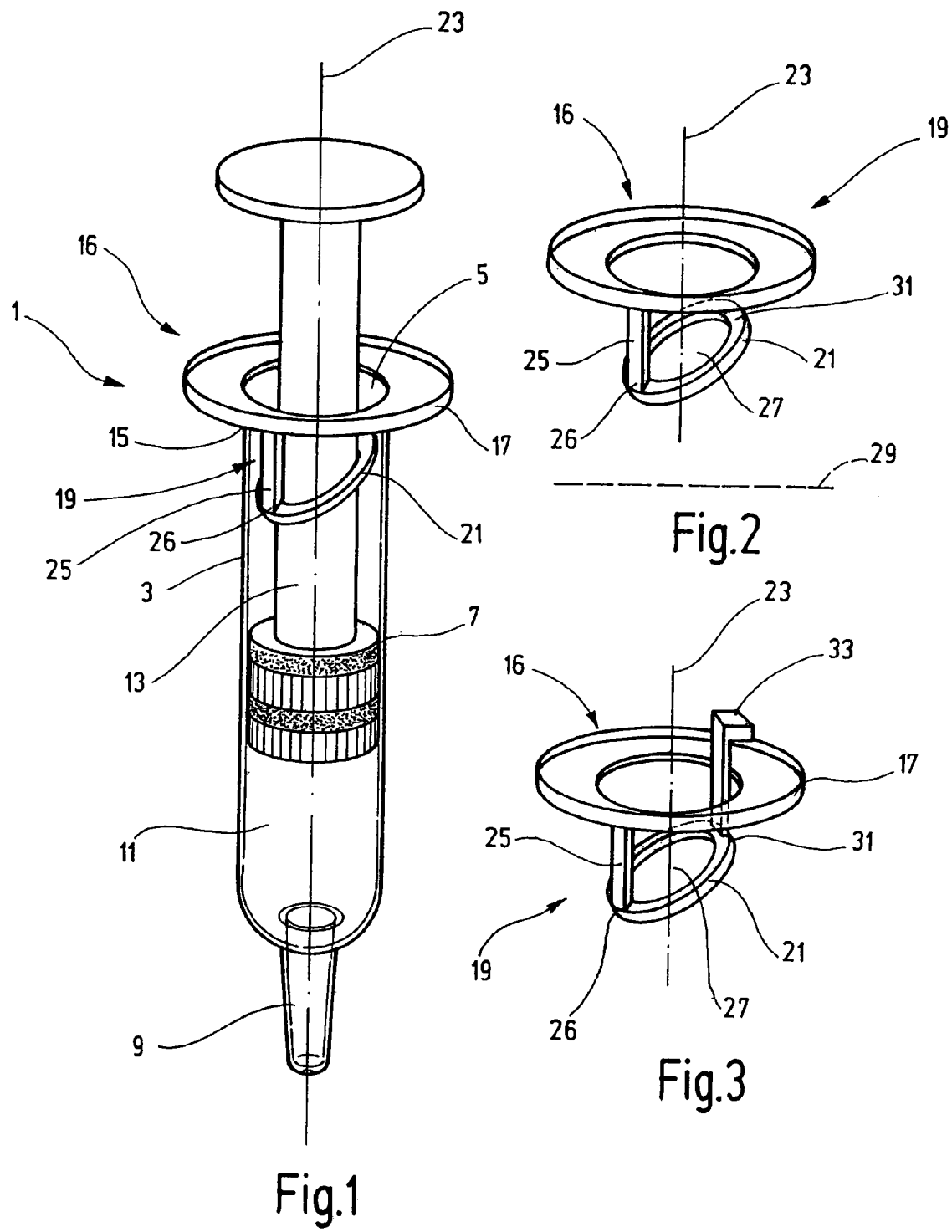

SYRINGE WITH INTERNAL SAFETY DEVICE

CROSS-REFERENCE TO RELATED APPLICATIONS

This application is a 371 National Stage of International Application No. PCT/EP2006/007927, filed Aug. 10, 2006. This application claims priority to German Patent Application No. 10 2005 037 962.1, filed 11 Aug. 2005. The disclosures of the above applications are herein expressly incorporated by reference.

FIELD

The invention relates to a syringe with a syringe cylinder filled with a medium, and with a sealing plug movably arranged within the syringe cylinder.

BACKGROUND

Syringes of the type discussed herein are known. It is known that with a loss of pressure, such as it occurs, for example, during the transport of syringes in air planes, the sealing plug in filled syringes migrates, even if only a small air bubble is present in the medium contained in the syringe cylinder. This leads to the sterility of the products present in the syringe cylinder being adversely affected.

It is therefore the task of the invention to create a syringe that does not have this disadvantage, i.e. which ensures the sterility of the products present in the syringe cylinder.

SUMMARY

A syringe is provided having a syringe cylinder filled with a medium, and furthermore a sealing plug movably disposed within the syringe cylinder, which serves to discharge the medium from the syringe cylinder, when necessary, in the known manner. The syringe is characterized by a safety device, which prevents the sliding back of the sealing plug in the syringe cylinder. It is therefore also not possible that the sealing plug moves, even in case of a loss of pressure, thereby crossing over the interior of the syringe cylinder, which may be contaminated. Due to this safety device it is no longer possible that the medium placed in the syringe cylinder, and sealed by the sealing plug, is contaminated.

One embodiment example of the invention is preferred, which is characterized in that the safety device comprises a locking element, which engages at the plunger, which cooperates with the sealing plug. Therefore, a relatively simple safety device can be realized, because the plunger is accessed more easily than the sealing plug itself.

Further, another embodiment example of the invention is preferred, which is characterized in that the locking element can be tilted. On one hand, it can therefore assume a releasing position when the sealing plug is moved into the plunger in the syringe cylinder. On the other hand, the locking element can be tilted from the releasing position into a locking position, when the sealing plug, and therefore also the plunger, want to perform opposite movements. For this purpose it is provided that the locking element comprises an angle of <90° with the center axis of the plunger, i.e. is positioned laterally as opposed to the center axis of the syringe. When this angle is changed, the locking element moves from the releasing position into a locking position, and vice versa. The syringe is very simple in its construction, and therefore not prone to failure.

Another embodiment example of the syringe is particularly preferred, which is characterized in that the locking element can be impinged with a pretensioning force, which forces it into the locking position. In this manner the safety of the sealing plug, having practically no clearance, against any undesired movement, is ensured.

Another embodiment example of the syringe is particularly preferred, which is characterized in that the locking element is embodied as a ring. This can ensure that the locking element grasps the plunger at two locations in such a manner that the sliding back of the sealing plug is safely avoided.

Another embodiment example of the syringe is particularly preferred, which is characterized in that the safety device comprises an unlocking element, with the aid of which the locking element can be displaced into the releasing position, and/or can be retained in the same. Despite of the safety device preventing any sliding back of the sealing plug it is also quite possible to purposefully displace the sealing plug if necessary, particularly to pull back the same.

Further embodiments are obvious from the sub-claims.

DRAWINGS

The invention is explained in further detail with regard to the drawing. It shows:

FIG. 1 a schematic diagram of a syringe in a perspective view,

FIG. 2 a first embodiment example of a safety device of a syringe according to FIG. 1, FIG. 3 a second embodiment example of a safety device.

DETAILED DESCRIPTION

The syringe 1 illustrated in FIG. 1 has a syringe cylinder 3, in the interior space 5 of which a sealing plug 7 is inserted in a movably displaceable manner. At its one end, at the bottom in FIG. 1, a syringe cylinder 3 with a needle attachment piece 9 is provided. It can be sealed using a suitable cover, if necessary, if a medium is placed within the syringe cylinder 3. Thereby a region 11 for receiving a medium can be formed below the sealing plug 7.

At the sealing plug 7 a plunger 13 engages, which protrudes from the open end of the syringe cylinder 1 opposite of the needle attachment piece 9. The region 11, which serves for receiving a medium, is closed by the sealing plug 7 opposite of the open end 15 so that with a closed needle attachment piece 9 the medium is safe from environmental influences, particularly from contamination.

At the upper end 15 of the syringe cylinder 3 a locking element 16 is provided, which is attached to the syringe cylinder 3, and is preferably firmly mounted. The locking element 16 is preferably embodied as a so-called backstop, and in turn prevents the sliding out of the sealing plug 7 from the syringe cylinder 3. In the embodiment example illustrated herein, the locking element 16 is embodied as a finger impression piece 17 in the form of a flange for improving manageability.

The syringe 1 further comprises a safety device 19, which serves to prevent any undesired sliding back of the sealing plug 7 in the interior of the syringe cylinder 3. Thus it has the effect that the sealing plug 7 can be unintentionally displaced into the direction towards the open end 15 of the syringe 1.

In the embodiment example illustrated here, the safety device 19 cooperates with the plunger 13. It has a locking element 21, which is tilted as opposed to the center axis 23 of the syringe 1, which also forms the center axis of the plunger 13, and which engages at the plunger 13. The safety device 19 further has a retaining fixture 25 in the form of an arm for the locking element 21. It is apparent from FIG. 1 that the locking element 21 is connected to the retaining fixture 25 at a connecting point 16, and that the same is located lower, i.e. closer to the sealing plug 7, than the opposite end of the locking element 21. The retaining fixture 25 retains the locking element 21 in the position illustrated here as a tilted position, as opposed to the center axis 23.

FIG. 1 shows that the retaining fixture 25 retains the locking element 21 exclusively at the connecting point 26 so that the same can be freely pivoted around the connecting point 26.

In FIG. 1 the retaining fixture 25 is illustrated as a bar extending parallel to the center axis 23 of the syringe 1, it therefore extends linearly in the direction of the displacement path, both of the sealing plug 7 and of the plunger 13. The resilience of the retaining fixture 25 in the direction of the center axis 23 is therefore relatively low. However, it is also possible to embody the retaining fixture 25 in a flexible manner, such as using a bar extending in wavy lines. For this purpose, it may be somewhat resilient due to the forces exerted from the bottom, i.e. from the direction of the needle attachment piece 9 so that the connecting point 26 is not overloaded, and the locking element 21 may not tear away from the retaining fixture 25.

The retaining fixture in turn may be part of the finger impression piece 17, or may be attached to the same. It is preferably embodied so that it forces the locking element 21 into the tilted position shown herein, i.e. impinges using a pretensioning force.

The pretensioning force may be realized in a simple manner in that the locking element 21 is attached at a predetermined position at the retaining fixture 25 so that the retaining fixture 25 forces the locking element 21 into a certain position. For example, it is possible to manufacture the retaining fixture 25 and the locking element 21 in one piece, particularly using the plastic injection molding process, in order to provide a defined position of the locking element 21 as opposed to the retaining fixture 25.

This type of realization of a pretensioning force is particularly inexpensive. In particular, it does not require any spring elements, which force the locking element 21 into a predetermined position. As mentioned, this leads to a particularly simple and inexpensive construction of the safety device 19.

The pretensioning force mentioned herein causes the locking element 21 of the safety device 19 to automatically go into a locking position, which prevents the sliding back of the plunger 13 independently of which position the plunger is located within the syringe cylinder 3. Thus, the sealing plug 7 is also prevented from sliding back in any position it may assume within the syringe cylinder 3. It is particularly advantageous that, as mentioned above, this sliding back is prevented automatically without requiring any additional spring elements, or such.

Generally, it is also possible to attach the retaining fixture 25, which in this example forms a bar extending parallel to the center axis 23, at the interior wall of the syringe cylinder 3, such as by means of gluing, or such. However, it has proven particularly advantageous to preferably manufacture the locking element 16 in one piece, in this example to combine the finger impression piece 17 with the safety device 19.

FIG. 2 shows the first embodiment example of the safety device 19 separately, i.e. without the syringe cylinder 3, the plunger 13, and the sealing plug 7. Equal parts are provided with the same reference numbers so that reference is made to FIG. 1 in this regard.

Here, it becomes obvious that the locking element 21 of the safety device is embodied as a closed ring, which starts at the retaining fixture 25, and is arranged in a tilting manner as opposed to the center axis 23. The locking element 21 encompasses an interior space 27, in this example also a circular area, which is arranged in a tilted manner to the center axis 23.

When the locking element 21 is forced towards the bottom, i.e. is pivoted around the attachment point 26 at the retaining fixture 25 towards the bottom in a clockwise direction, the projection of the interior space 27 is increased to an imagined plane 29, on which the center axis 23 is perpendicular. By means of this interior space 27, which is increased due to the pivoting movement, the plunger 13 can be displaced towards the bottom, i.e. in FIG. 1 into the direction of the needle attachment piece 9. The pivoting movement of the locking element 21 towards the bottom into a releasing position occurs in this example by means of the friction forces between the locking element 21 and the plunger 13 penetrating through the same. Here, it is shown that with a displacement of the plunger 13 into the direction of the needle attachment piece 19, the locking element 21 is automatically pivoted into its releasing position. Thus, no additional measures or actuating elements are required to displace the locking element 21 into this releasing position.

When the plunger 13 is displaced into the opposite direction towards the top, the locking element 21 pivots towards the top in a counter-clockwise direction around the attachment point 26 toward the retaining fixture 25 due to the friction forces between the locking element 21 and the plunger 13, and particularly due to the pretensioning force of the retaining fixture 25. In this manner, the projection of the interior space 27 becomes smaller at the plane 19, the locking element 21, therefore catches the plunger 13 so that an upwards movement towards the top, i.e. away from the needle attachment piece 9, is prevented. Thus, if the locking element 21 is pivoted towards to top in a counter-clockwise direction around the attachment point 26 toward the retaining fixture 25, the locking element 21 moves into its locking position.

FIG. 2 shows that the locking element 21 engages at the exterior surface of the plunger 13 with its end 31 facing away from the attachment point 26 at the retaining fixture 25, if it is pivoted into its locking position towards the top. In the locking position, the locking element 21 can also stop and catch in the region of the attachment point 26 at the plunger 13. The retaining fixture 25 is embodied in this example such that the locking element 21 is forced into the locking position by means of pretensioning forces.

It becomes obvious that the locking element 21 does not need to be embodied as a closed ring, as illustrated in this example. It suffices, if the locking element 21, coming from the attachment point 26 at the retaining fixture 25, reaches laterally towards the top, and at the side opposite of the attachment point 26 at the exterior of the plunger 13 engages at the same as soon as the locking element 21 is pivoted into its locking position in counter-clockwise direction, and/or is forced by means of the pretensioning force. Instead of a closed ring with a circular or elliptical contour, a C-shaped locking element 21 could also be realized, or even a locking element having three essentially U-shaped side pieces, of which two extend essentially parallel to a base. One of the parallel side pieces is attached at the attachment point 26 of the retaining fixture 25, the other engages at the exterior surface of the plunger 13 at the side opposite of the attachment point 26 in order to prevent a displacement of the plunger towards the top in the locking position of the locking element 21.

The exemplifications as to the locking element 21 show that preferably the exterior contour of the plunger 13 and the interior contour of the locking element 13 are adjusted to each other in order to achieve optimum retaining forces when the locking element 21 is pivoted into its locking position. The plunger 13 can be composed of multiple individual bars. It is known, for example, to provide four bars located perpendicularly on top of each other in order to realize the basic body of the plunger 13. However, more than four such bars may also be used. Furthermore, the plunger 13 may be manufactured as a solid or hollow body, having a circular or oval contour.

The following becomes obvious from the exemplifications: the locking element 21 is retained by the retaining fixture 26 in such a manner that it is preferably forced into its locking position. In this position, the plunger 13 cannot be unintentionally displaced towards the top, i.e. in FIG. 1 away from the needle attachment piece 9. If the plunger 13 is pulled, the locking element 21 thereby pivots further towards the top around the attachment point 26, thereby decreasing the interior space 27, and leading to an increased retaining force at the plunger 13. With a movement of the plunger towards the bottom, the locking element 21 is pivoted around the attachment point 26 in a clockwise position, because the exterior of the plunger 13 builds friction forces at the interior of the locking element 21. By means of this pivoting movement, the projection of the interior 27 is increased at a plane 29, i.e. the free space within the locking element 21; the same is thus pivoted towards the bottom into its releasing position with a movement of the plunger 13.

FIG. 3 shows a modified embodiment example of the safety device 19. Equal parts are provided with the same reference numbers so that reference is made to FIGS. 1 and 2 as to the description.

The only difference of the safety device 19 according to FIG. 3 as opposed to the safety device 19 according to FIG. 2 is that an unlocking element 33 is provided at the locking element 21. If a force is exerted on the same from the top, the locking element 21 is pivoted towards the bottom, i.e. in clockwise position, around the attachment point 26, and is displaced into its releasing position. If the force exerted upon the unlocking element 33 is greater than the pretensioning force and the friction forces between the exterior of the plunger 13 and the interior of the locking element 21, the locking element 21 is retained in the releasing position. In this manner, the plunger 13 can also be displaced towards the top, if necessary, i.e. in the direction of the open end 15 of the syringe cylinder 13, even if the safety device is inserted in the same.

The unlocking element 33 therefore allows that the automatic effect of the safety device 19, which prevents any unintentional displacement of the plunger 13, and thus also of the sealing plug 7, towards the top, is cancelled, and to pull the sealing plug 7 towards the top together with the plunger 13. Due to the fact that the sealing element 16 is embodied as a backstop, the sealing plug 7 may not be completely pulled out of the syringe cylinder 3, even when the safety device 19 is unlocked.

Preferably, the unlocking element 33 engages at the free end 31 of the locking element 21, i.e. on the side opposite of the attachment point 26. In this manner, the forces required for unlocking the locking element 31 are reduced to a minimum.

In the embodiment example illustrated in FIG. 3, the unlocking element 33 protrudes over the finger impression piece 17 towards the top. Thus, it is freely accessible to a user of the syringe 1. It is also possible to place the free end of the unlocking element 33 facing away from the locking element 21 into the interior space 5 of the syringe cylinder 3 so that the unlocking of the safety device 19 is possible only by means of a tool. This increases the safety of the safety device 19 described herein.

The safety device 19 is preferably made of plastic, and can be manufactured particularly using the injection molding method. This substantially reduces costs for the manufacture of the safety device 19. It is particularly advantageous if the finger impression piece 17 and the safety device 19 are both manufactured of the same material and are realized as one piece.

However, it is generally also quite possible to manufacture the locking element 21 of metal or of a composite material in order to realize a particularly good engagement on the exterior of the plunger 13. In this manner, a particularly great safety against any unintentional displacement of the sealing plug 7 and of the plunger 13 is ensured.

In order to improve the engagement of the locking element 21 on the exterior of the plunger 13 it is possible to embody the exterior surface of the plunger 13 with a certain roughness so that the locking element 21 already catches at the plunger 13 with the slightest upwards movement. The interior of the locking element 21 facing the interior space 27 may also be embodied respectively rough in order to increase the catching forces, and therefore the securing force.

It is obvious from the explanations as to the operation of the safety device 19, in particularly of the locking element 21 that the safety device 19 may also have multiple locking elements, for example also rings, which cooperate in the sense discussed herein with the plunger 13, and prevent the sliding back of the plunger 13, and therefore also of the sealing plug 7.

What is claimed is:

1. A syringe comprising:
    a syringe cylinder including a proximal end having an opening and a distal end having a needle attachment piece;
    a sealing plug movably disposed within the syringe cylinder;
    a plunger received within the opening and cooperating with the sealing plug; and
    a safety device disposed within the syringe cylinder that prevents a sliding back of the sealing plug within the syringe cylinder in any position the sealing plug assumes within the syringe cylinder, the safety device including a retaining fixture and a locking element, the retaining fixture distally extending into the syringe cylinder from proximate the proximal end, the locking element carried at a distal end of the retaining fixture and operative to engage the plunger in any position the plunger assumes within the syringe cylinder;
    wherein the locking element is attached to the retaining fixture and protrudes from the retaining fixture in such a manner that an attachment point of the locking element is closer to the sealing plug at the retaining fixture than the free end of the locking element opposite of the attachment point;
    wherein the locking element is pivotally coupled to the retaining fixture at the attachment point, the locking element assumes a releasing position when the plunger is pushed into the syringe cylinder and a locking position when the plunger is moved in an opposite direction, wherein the locking element defines an angle of 90° with a center axis of the plunger, which is larger in the releasing position than in the locking position, the angle opening towards the upper end of the syringe cylinder opposite of the needle attachment piece.

2. The syringe according to claim 1, wherein the retaining fixture of the locking element retains exclusively at the attachment point so that the locking element is freely movable around the attachment point.

3. The syringe according to claim 1, wherein the retaining fixture is embodied in a flexible manner in the direction of the displacement path of the sealing plug and of the plunger.

4. The syringe according to claim 1, wherein the free end is proximally biased into engagement with the plunger.

5. The syringe according to claim 1, wherein the retaining fixture is attached to a closure element for the syringe cylinder.

6. The syringe according to claim 1, wherein the sealing closure prevents the pulling out of the sealing plug from the syringe cylinder.

7. The syringe according to claim 5, wherein the closure element is embodied as a finger impression piece.

8. The syringe according to claim 1, wherein the free end of the locking element opposite the attachment point moves toward the proximal end of the syringe cylinder from the releasing position to the locking position.

9. The syringe according to claim 1, wherein the locking element is impinged with a pretensioning force, which forces the locking element into the locking position.

10. The syringe according to claim 1, wherein the locking element is firmly attached to the retaining fixture in a defined angular position, and is forced into the defined position by the retaining fixture.

11. The syringe according to claim 1, wherein friction forces are exerted between the locking element and the exterior of the plunger, due to which the locking element is displaced into its releasing position with a displacement of the plunger in a direction toward the needle attachment piece.

12. The syringe according to claim 1, wherein the locking element encompasses the plunger in such a manner that it cooperates with the plunger in the locking position at two locations.

13. The syringe according to claim 1, wherein the locking element is a ring.

14. The syringe according to claim 1, further comprising an unlocking element for displacing the locking element into the releasing position.

15. The syringe according to claim 14, wherein the unlocking element engages at the free end of the locking element.

16. The syringe according to claim 14, wherein the unlocking element protrudes from an interior of the syringe cylinder over a closure element for the syringe cylinder.

17. The syringe according to claim 1, further comprising an unlocking element for retaining the locking element.

18. A syringe comprising:
a syringe cylinder having a proximal end having an opening and a distal end having a needle attachment piece;
a sealing plug movably disposed within the syringe cylinder;
a plunger received within the opening and cooperating with the sealing plug; and
a safety device including a flange positioned proximate a proximal end of the syringe cylinder, an arm distally extending from the flange and into the cylinder and a ring pivotally coupled at an attachment point to a distal end of the arm and surrounding the plunger, a free end of the ring opposite the attachment point being biased into engagement with the plunger.

19. The syringe according to claim 18, wherein the ring defines an opening having a diameter smaller than a diameter of the sealing plug.

20. The syringe according to claim 18, wherein the ring is disposed in a plane at an angle to the flange.

21. The syringe according to claim 18, wherein the ring is pretensioned to prevent sliding back of the plunger independent of the plunger position within the cylinder.

22. A syringe comprising:
a plunger carrying a sealing plug;
a syringe cylinder having a proximal end for receiving the plunger and a distal end; and
a safety device disposed within the syringe cylinder that prevents a sliding back of the sealing plug within the syringe cylinder in any position the sealing plug assumes within the syringe cylinder, the safety device having a retaining fixture distally extending into the syringe cylinder and a locking ring surrounding the plunger and pivotally coupled to the retaining fixture at an attachment point proximate a distal end of the retaining feature, a free end of the locking ring opposite the attachment point positioned closer to the proximal end of the cylinder than the attachment point.

23. The syringe according to claim 22, wherein the locking ring can be tilted, and assumes a releasing position when the plunger is pushed into the syringe cylinder, and a locking position when the plunger is moved in the opposition direction, wherein the locking element encompasses an angle of <90° with a center axis of the plunger, which is larger in the releasing position than in the locking position, the angle opening towards the upper end of the syringe cylinder opposite of the needle attachment piece.

24. The syringe according to claim 22, wherein the locking ring is biased into engagement with the plunger.

* * * * *